US011432729B2

(12) United States Patent
Yoshino et al.

(10) Patent No.: US 11,432,729 B2
(45) Date of Patent: Sep. 6, 2022

(54) BLOOD PRESSURE INFORMATION MEASUREMENT APPARATUS CUFF AND BLOOD PRESSURE INFORMATION MEASUREMENT APPARATUS

(71) Applicant: OMRON HEALTHCARE Co., Ltd., Kyoto (JP)

(72) Inventors: Hiroko Yoshino, Kyoto (JP); Naomi Matsumura, Kyoto (JP); Masahiro Kobayashi, Kyoto (JP); Wataru Tsunoda, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 756 days.

(21) Appl. No.: 16/273,602

(22) Filed: Feb. 12, 2019

(65) Prior Publication Data

US 2019/0167127 A1    Jun. 6, 2019

Related U.S. Application Data

(60) Division of application No. 14/644,962, filed on Mar. 11, 2015, now abandoned, which is a continuation of
(Continued)

(30) Foreign Application Priority Data

Sep. 25, 2012  (JP) .................. 2012-211137

(51) Int. Cl.
| | | |
|---|---|---|
| *A61B 5/022* | (2006.01) | |
| *B29C 53/40* | (2006.01) | |
| *B29C 65/00* | (2006.01) | |
| *A61B 5/00* | (2006.01) | |

(52) U.S. Cl.
CPC .......... *A61B 5/02233* (2013.01); *B29C 53/40* (2013.01); *A61B 5/6824* (2013.01); *B29C 66/43121* (2013.01)

(58) Field of Classification Search
None
See application file for complete search history.

(56) References Cited

U.S. PATENT DOCUMENTS

| | | | |
|---|---|---|---|
| 4,979,953 A | 12/1990 | Spence | |
| 7,758,607 B2 * | 7/2010 | McEwen | ............. A61B 17/135 606/202 |

(Continued)

FOREIGN PATENT DOCUMENTS

| | | |
|---|---|---|
| JP | H02-299635 A | 12/1990 |
| JP | H04-67837 A | 3/1992 |

(Continued)

OTHER PUBLICATIONS

United States Office Action in related U.S. Appl. No. 14/644,962. dated Jan. 30, 2020 (15 pages).

(Continued)

*Primary Examiner* — Barbara J Musser
(74) *Attorney, Agent, or Firm* — Osha Bergman Watanabe & Burton LLP

(57) ABSTRACT

A method for manufacturing a blood pressure information measurement apparatus includes the following steps: forming a hole in a flexible resin sheet; inserting a connecting pipe into the hole; overlaying a first end portion and a second end portion of the flexible resin sheet such that an inner side of the first end portion contacts an outer side of the second portion; welding a location at which the first end portion and the second end portion overlap to form a first welded portion, such that the flexible resin sheet forms a tube-shaped body having a first end and a second end; flattening the tube-shaped body; welding the first end and the second to form two second welded portions, such that the tube-shaped body forms a bladder having two long sides and two short sides; and welding portions of the resin sheet which
(Continued)

overlap along a first long side to form one or more partial welded portions.

2 Claims, 12 Drawing Sheets

Related U.S. Application Data application No. PCT/JP2013/071528, filed on Aug. 8, 2013.

(56) References Cited

U.S. PATENT DOCUMENTS

| 2001/0020133 | A1 | 9/2001 | Ito |
| 2004/0181156 | A1 | 9/2004 | Kingsford et al. |
| 2006/0027946 | A1* | 2/2006 | Kawamura ......... B29C 66/1122 264/239 |

FOREIGN PATENT DOCUMENTS

| JP | H05-64631 A | 3/1993 |
| JP | 2003-052651 A | 2/2003 |
| JP | 2006-130331 A | 5/2006 |

OTHER PUBLICATIONS

Office Action dated Aug. 7, 2020 in the related U.S. Appl. No. 14/644,962 (15 pages).
International Search Report issued in Application No. PCT/JP2013/071528, dated Oct. 1, 2013 (1 page).
International Preliminary Report on Patentability issued in Application No. PCT/JP2013/071528, dated Mar. 25, 2015 (17 pages).

* cited by examiner

BLOOD PRESSURE INFORMATION MEASUREMENT APPARATUS CUFF AND BLOOD PRESSURE INFORMATION MEASUREMENT APPARATUS

CROSS-REFERENCE TO RELATED APPLICATIONS

This application is a divisional application of U.S. patent application Ser. No. 14/644,962 filed Mar. 11, 2015, now abandoned, which is a continuation application of PCT application No. PCT/JP2013/071528 filed Aug. 8, 2013, and claims priority to Japanese Patent Application No. 2012-211137 filed Sep. 25, 2012, the contents of which are hereby incorporated by reference in their entirety.

TECHNICAL FIELD

The present invention relates to a blood pressure information measurement apparatus cuff and a blood pressure information measurement apparatus.

BACKGROUND ART

A blood pressure information measurement apparatus acquires blood pressure information such as a pulse wave and a blood pressure value of a measurement subject. When blood pressure information is to be measured using the blood pressure information measurement apparatus, a cuff containing a fluid bladder that pressurizes an artery in a body is first wrapped around a surface of the body. Then, the fluid bladder inside the wrapped cuff is inflated/deflated, and an arterial pressure pulse wave occurring in an artery is detected. Then, various types of blood pressure values are detected based on the detected pulse wave.

Here, "cuff" refers to a belt-shaped structure that has an inner cavity and can be wrapped around a portion of a body, and it indicates an object that is used for measurement of arterial pressure in upper or lower extremities and the like by insertion of a fluid such as air or a liquid into the inner cavity. Accordingly, "cuff" indicates a concept including a fluid bladder and a wrapping means for wrapping the fluid bladder around a body.

A blood pressure information measurement apparatus cuff is provided with a bag-shaped cover body containing an air bladder serving as a fluid bladder. The bag-shaped cover body is normally formed into a bag shape by overlaying two sheet-shaped members composed of an inner cover and an outer cover and bonding the circumferential edges thereof together. Structures of cuffs containing this kind of air bladder are disclosed in Patent Documents 1 and 2, for example.

In the blood pressure information measurement apparatus cuffs disclosed in Patent Document 1 and Patent Document 2, the contained air bladder is manufactured as follows. That is to say, the ends of two opposing side portions (long sides) of a rectangular resin sheet are overlapped and welded together so as to form a tube shape, and the resin sheet, which is now a tube-shaped body, is flattened so that the two side portions (short sides), which form openings on both sides, are welded. Accordingly, an air bladder having a structure in which both ends are blocked is obtained.

CITATION LIST

Patent Literature

Patent Document 1: JP H4-67837A
Patent Document 2: JP 2003-52651A

SUMMARY OF INVENTION

In the cuff with the foregoing structure, an air bladder 1 is formed into a long, narrow shape as shown in FIG. 12A. Two sides 3 and 3, which are the long sides of the air bladder 1, are formed by one resin sheet being folded. For this reason, if an external force in the direction of arrow A is applied to the air bladder 1, the air bladder 1 will easily roll in the direction in which the external force acts, causing lateral shifting to occur. In other words, as shown in FIG. 12B in the cross section taken along line P-P in FIG. 12A, the long side 3 of the air bladder 1 is extended in direction a1 in which the external force is received, or is retracted in direction a2, and thus the position thereof in the direction of arrow A changes.

If lateral shifting occurs in the air bladder 1, the pressurization point on the measurement site on the body surface will shift, causing a loss of pressurization force, whereby it is less likely that a sufficient pressurization force will be caused to act on the measurement site. As a result, there is a risk that accurate blood pressure information will not likely be obtained.

Therefore, one or more embodiments of the claimed invention provide a blood pressure information measurement apparatus cuff and a blood pressure information measurement apparatus according to which a sufficient pressurization force can be caused to act on a measurement site, using a simple configuration.

One or more embodiments of the claimed invention have the following configuration.

According to one or more embodiments of the claimed invention, a blood pressure information measurement cuff includes a belt-shaped cuff body and a fluid bladder that is attached to the cuff body and is configured to expand and contract with insertion and discharge of a fluid, the blood pressure information measurement cuff being configured to be used while wrapped around a body being examined.

According to one or more embodiments of the claimed invention, the fluid bladder is formed into a rectangular bag shape by flattening a tube-shaped resin sheet and sealing two end portions thereof that form openings, and partial welded portions, which are each formed by the resin sheet being folded such that it overlaps itself and welded, are formed on at least a portion of one of a pair of opposing sides that intersect the two sealed end portions and extend along a wrapping direction on the body being examined.

According to one or more embodiments of the claimed invention, a blood pressure information measurement apparatus includes the blood pressure information measurement cuff; an expansion/contraction mechanism configured to cause the fluid bladder to expand and contract; and a blood pressure information acquisition unit configured to acquire blood pressure information.

According to one or more embodiments of the claimed invention, a sufficient pressurization force can be caused to act on a measurement site with a simple configuration, and high-accuracy blood pressure measurement can be performed.

DETAILED DESCRIPTION OF INVENTION

Hereinafter, one or more embodiments of the claimed invention will be described in detail with reference to the drawings.

Figure 1:
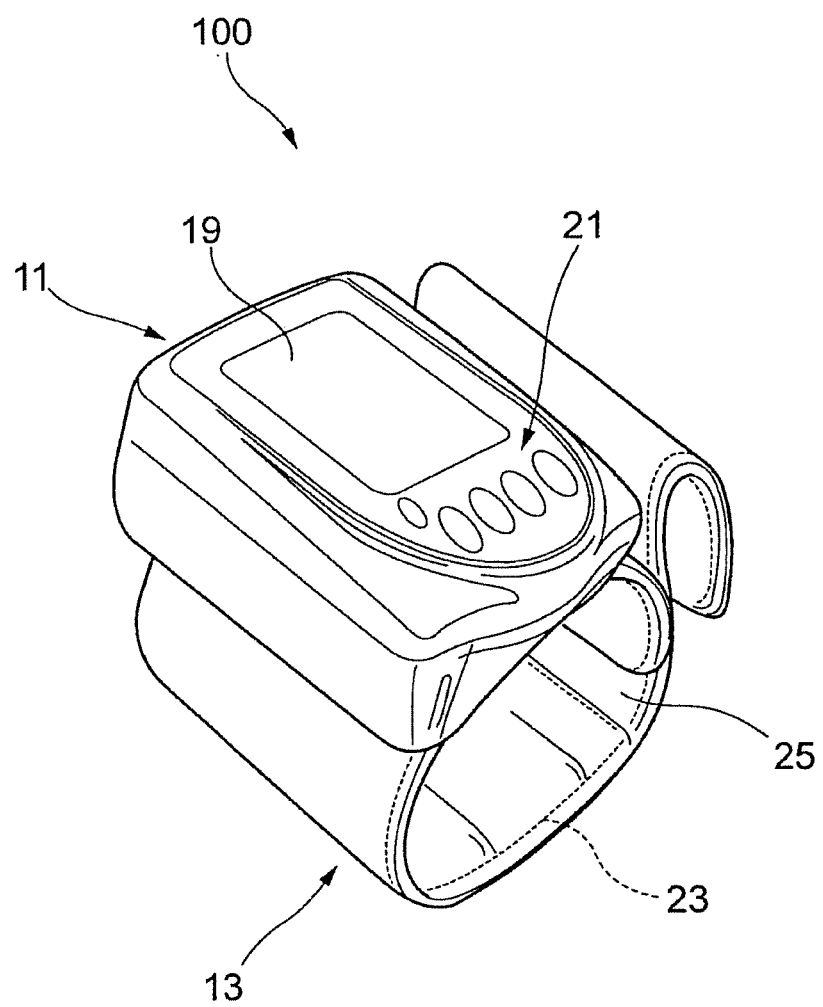
FIG. 1 is a diagram for describing an embodiment of the invention and an overall configuration diagram showing a configuration of a blood pressure information measurement apparatus.

FIG. 1 is a diagram for describing an embodiment of the invention and an overall configuration diagram showing a configuration of a blood pressure information measurement apparatus.

A blood pressure information measurement apparatus (abbreviated as "blood pressure meter" below) 100 mainly includes an apparatus body 11 serving as a blood pressure information acquisition unit, and a blood pressure meter cuff (abbreviated as "cuff" below) 13. The illustrated blood pressure meter 100 is a wrist-type blood pressure information measurement apparatus configured to measure blood pressure information such as a blood pressure value in a state in which the cuff 13 is attached to a wrist of a measurement subject.

Examples of blood pressure information include a blood pressure value, a pulse waveform, a pulse count, and the like, and a systolic blood pressure value, a diastolic blood pressure value, a pulse rate, a pulse wave amplitude, an AI (Augmentation Index) value, a TR (Time of Reflection) value, and the like, which are calculated using the blood pressure value, the pulse waveform, the pulse count, and the like.

The apparatus body 11 and the cuff 13 are in an integrated configuration, and the apparatus body 11 and the cuff 13 are connected via an air passage (not shown) from an air connection opening provided on the cuff 13 side to the apparatus body 11.

The apparatus body 11 is provided with a display unit 19 for information display, and an input operation unit 21 that receives input of various information. The display unit 19 uses numeric values, a graph, and the like to visibly display measurement results and the like of the blood pressure value and the pulse rate. For example, a liquid crystal panel and the like are used as the display panel 19. The input operation unit 21 is provided with a power supply button, a measurement start button and various buttons for inputting information relating to the measurement subject.

The cuff 13 is formed in an overall band shape, and is used while wrapped around a wrist of the measurement subject. The cuff 13 has an air bladder 23, which is a fluid bladder for pressurizing the wrist, and a bag-shaped cover body 25 serving as a cuff body for attaching the air bladder 23 to a wrist of the measurement subject by being wrapped around a wrist of the measurement subject.

Figure 2:
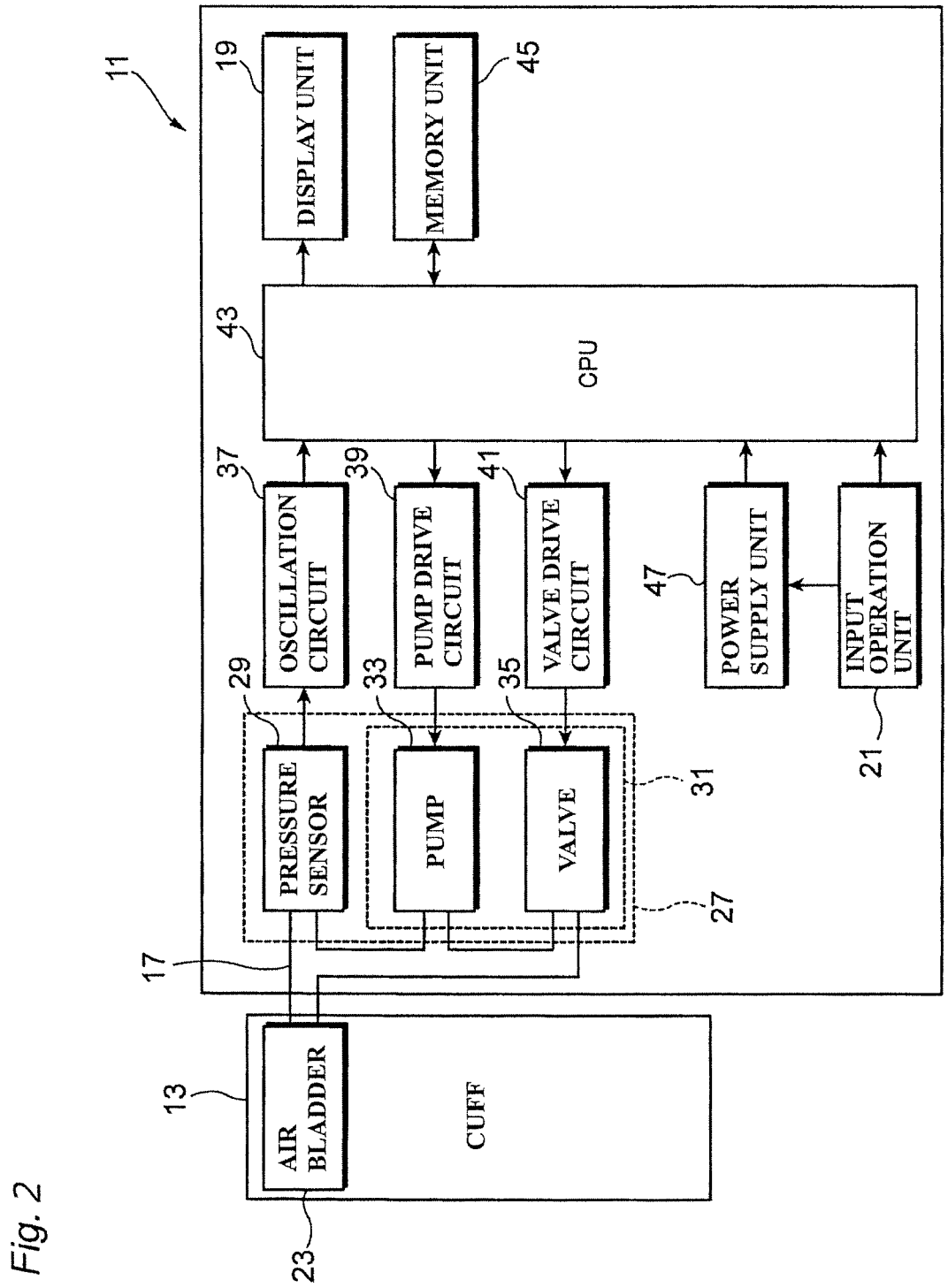
FIG. 2 is a functional block diagram of the blood pressure information measurement apparatus according to one or more embodiments of the claimed invention.

FIG. 2 is a functional block diagram of the blood pressure information measurement apparatus shown in FIG. 1.

The apparatus body 11 is provided with a blood pressure measurement air system component 27 for supplying air to or discharging air from the air bladder 23 contained in the cuff 13. The blood pressure measurement air system component 27 has a pressure sensor 29 that detects the pressure in the air bladder 23, and a pump 33 and a valve 35, which are an expansion/contraction mechanism 31 that causes the air bladder 23 to expand/contract. Inside of the apparatus body 11, an oscillation circuit 37, a pump drive circuit 39, and a valve drive circuit 41 are provided in association with the blood pressure measurement air system component 27.

The apparatus body 11 is provided with a CPU (Central Processing Unit) 43 serving as a control unit that performs overall control and monitoring of the units in a focused manner, a memory unit 45 for storing programs that cause the CPU 43 to perform predetermined operations and various types of information such as measured blood pressure values, the display unit 19 and input operation unit 21, and a power supply unit 47 that supplies electricity serving as a power supply to the CPU 43. The CPU 43 functions also as a blood pressure value calculation means for calculating a blood pressure value.

The blood pressure sensor 29 detects the pressure in the air bladder 23 (hereinafter referred to as "cuff pressure") and outputs a signal corresponding to the detected cuff pressure to the oscillation circuit 37. The pump 33 supplies air to the air bladder 23. The valve 35 performs an opening/closing operation when the pressure in the air bladder 23 is to be maintained or the air in the air bladder 23 is to be discharged. The oscillation circuit 37 outputs a signal having an oscillation frequency that corresponds to the output value of the pressure sensor 29 to the CPU 43. The pump drive circuit 39 controls the driving of the pump 33 based on a control signal obtained from the CPU 43. The valve drive circuit 41 performs control of opening/closing the valve 35 based on a control signal obtained from the CPU 43.

Figure 3:
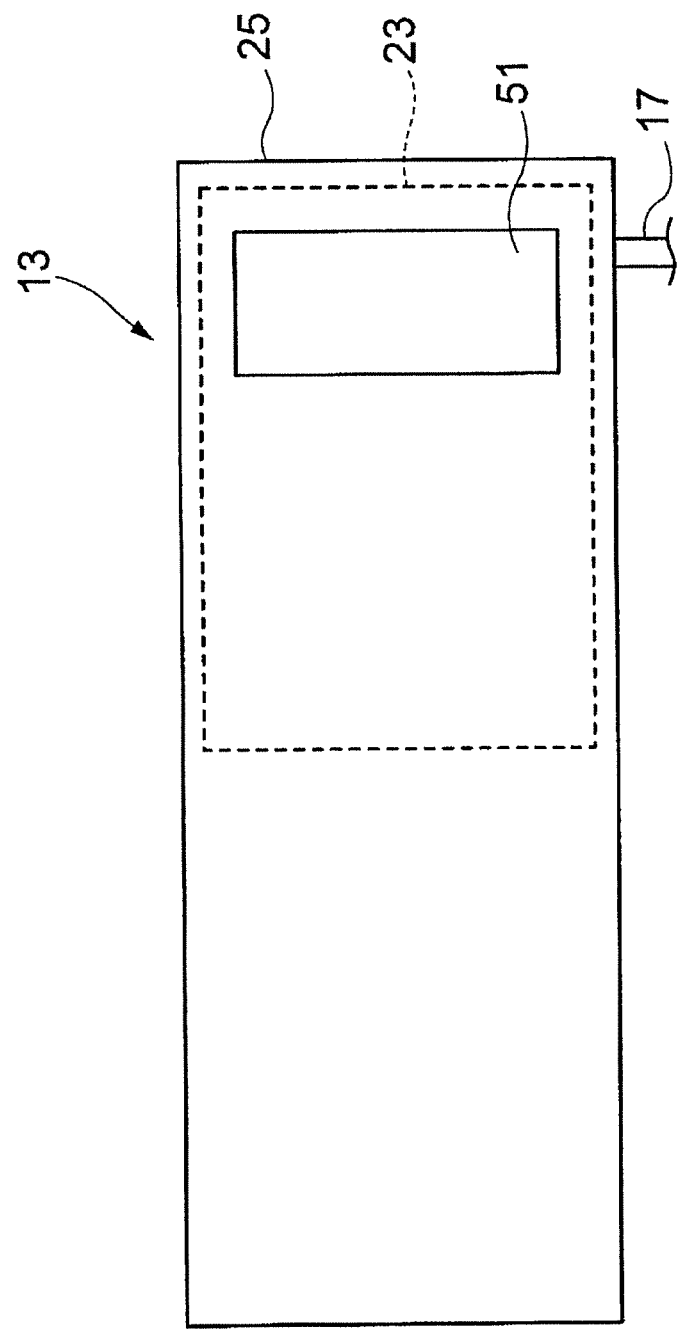
FIG. 3 is a plan view showing a cuff body.

FIG. 3 is a plan view of the cuff 13. The cuff 13 has the air bladder 23 and the bag-shaped cover body 25. The bag-shaped cover body 25 is formed into a bag shape by overlaying two sheet-shaped members composed of an inner cover and an outer cover and bonding the circumferential edges thereof together. A surface fastener 51 composed of Magic Tape (registered trademark), for example, is provided on the exterior of the cuff 13 and the air bladder 23.

Figure 4:
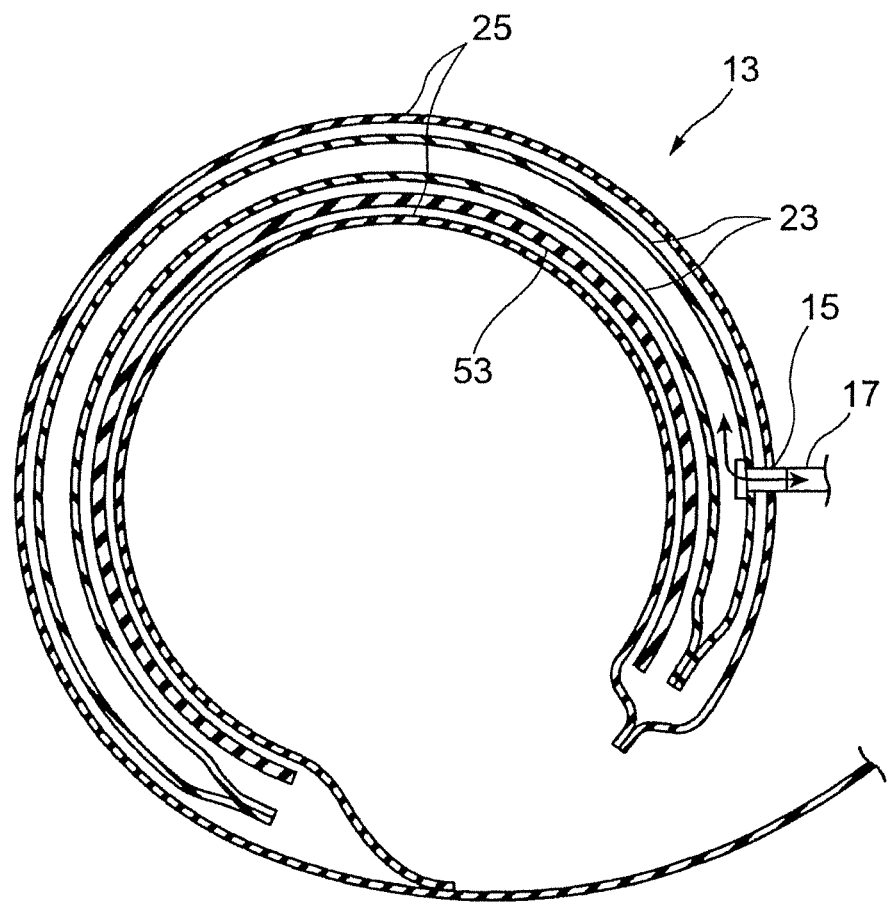
FIG. 4 is a cross-sectional view of the cuff body.

FIG. 4 is a cross-sectional view showing a state in which the cuff 13 is wrapped around a wrist of the measurement subject. In the cuff 13, a curler 53 may be provided between the air bladder 23 and the bag-shaped cover body 25. The curler 53 is composed of a flexible member that is configured to be able to undergo elastic deformation in the diameter direction by being wrapped circularly. The curler 53 is adhered/fixed to the outer circumferential face of the air bladder 23 via an adhering member such as double-sided tape (not shown), and is configured to extend along the wrist by maintaining its annular form. The curler 53 is for making the cuff 13 easier for the measurement subject to attach to his/her wrist and is for biasing the air bladder 23 toward the inner side of the wrist when the cuff 13 is attached to the wrist. Note that the curler 53 is formed by a resin material such as polypropylene (PP) for example, so as to exhibit sufficient elastic force.

Next, a method for manufacturing the above-described air bladder 23 will be described.

Figure 5A:
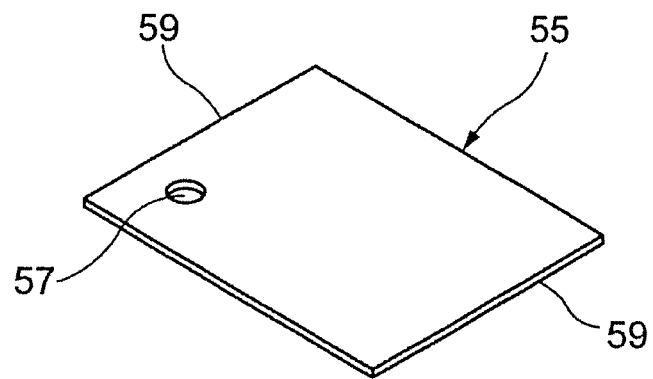
FIG. 5A is a diagram illustrating a method for manufacturing a fluid bladder.

FIGS. 5A, 5B, 5C, and 5D are diagrams illustrating a method for manufacturing the air bladder 23. In the method for manufacturing the air bladder 23, first, as shown in FIG. 5A, one rectangular resin sheet 55 is prepared. The resin sheet 55 is a flexible sheet composed of, for example, ethylene-vinyl acetate copolymer (EVA), flexible polyvinyl chloride (PVC), polyurethane (PU), natural rubber (NR), or the like. A hole 57 for attaching a connecting pipe 17 is drilled in a portion of the resin sheet 55.

Figure 5B:
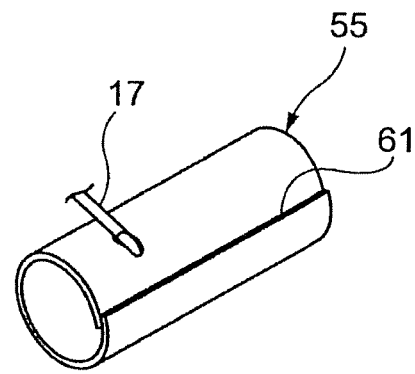
FIG. 5B is a diagram illustrating a method for manufacturing a fluid bladder.

Next, the connecting pipe 17 is inserted into the hole 57 provided in the resin sheet 55, and thereafter, as shown in FIG. 5B, the two end portions 59 and 59 of the two opposing sides of the resin sheet 55 are overlaid such that the inner face of one of the two end portions 59 and 59 is in contact with the outer face of the other end, and the location at which they overlap is welded using a high-frequency welder or the like. Accordingly, the resin sheet 55 becomes a tube-shaped body and a first welded portion 61 is formed along the axis direction of the tube-shaped body.

Figure 5C:
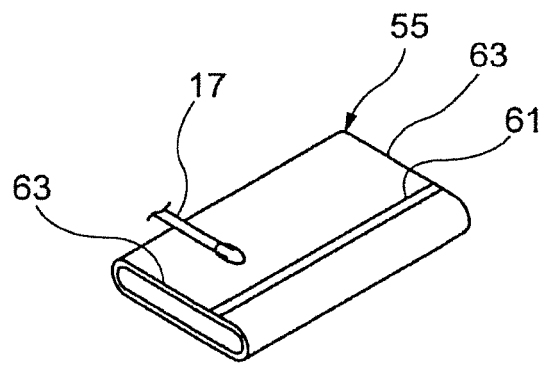
FIG. 5C is a diagram illustrating a method for manufacturing a fluid bladder.
Figure 5D:
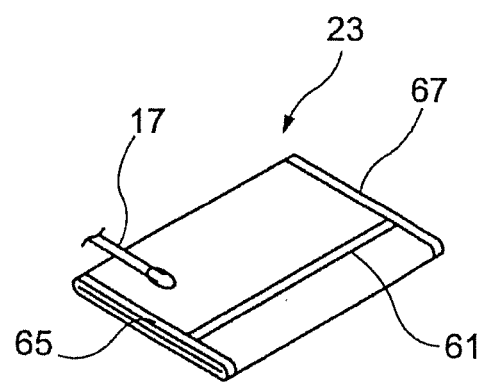
FIG. 5D is a diagram illustrating a method for manufacturing a fluid bladder.

Next, as shown in FIG. 5C, the tube-shaped body processed in FIG. 5B is flattened. The flattened resin sheet 55 has openings on the two ends 63 and 63 of the tube-shaped body. As shown in FIG. 5D, the two ends 63 and 63 at which the openings are formed are welded using a high-frequency welder or the like so as to form second welded portions 65 and 67. The air bladder 23 manufactured in the manner described above is rectangular in plan view and is contained in the cuff 13 such that the long-side portions extend in the circumferential direction when wrapped around the wrist, and the short-side portions extend in the longitudinal direction, which is orthogonal to the circumferential direction. The length of the long-side portions is greater than or equal to 100 mm and less than or equal to 220 mm, for example, and the length of the short-side portions can be a length that is greater than or equal to 40 mm and less than the length of the long-side portion, for example. Note that the air bladder 23 can also be square-shaped, another polygonal shape, or the like.

Next, an air bladder in which further machining is performed so as to make lateral shifting less likely will be described with respect to the air bladder 23 manufactured using the above-described method. In the following description, members and sites that are the same are denoted by the same reference numerals, and the description thereof will be omitted or simplified.

First Configuration Example

Figure 6:
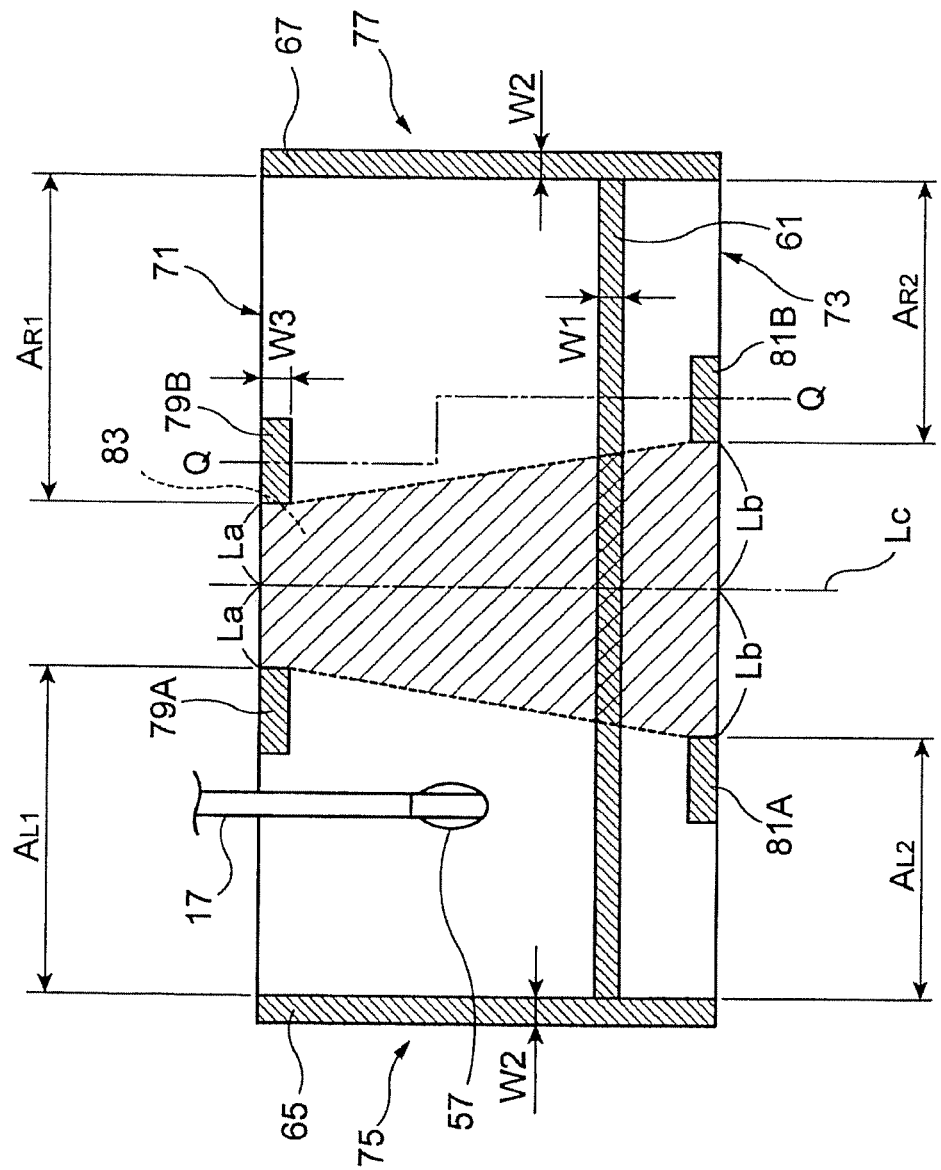
FIG. 6 is a plan view of an air bladder according to a first configuration example.

FIG. 6 is a plan view of an air bladder according to a first configuration example. An air bladder 23A of the present configuration example has long sides 71 and 73, which are a pair of opposing sides extending in the wrapping direction on the measurement subject, and a pair of short sides 75 and 77 that extend in a direction orthogonal to the wrapping direction. The air bladder 23A is formed so as to be rectangular in plan view. The aforementioned first welded portion 61 and second welded portions 65 and 67 are formed on the air bladder 23A.

In addition to the first welded portion 61 and the second welded portions 65 and 67, partial welded portions 79A, 79B, 81A, and 81B, which are formed by the resin sheet 55 being folded such that it vertically overlaps itself in portions of the long sides 71 and 73 and being welded at those portions, are formed on the air bladder 23A. The partial welded portions 79A and 79B are formed on the long side 71, and the partial welded portions 81A and 81B are formed on the long side 73.

That is to say, the air bladder 23A is formed into a rectangular bag shape by flattening the tube-shaped resin sheet and closing the two end portions that form openings. The partial welded portions 79A, 79B, 81A, and 81B, which are formed by the resin sheet being folded such that it overlaps itself and welded, are formed on at least a portion of one (both in the present embodiment) of the long sides 71 and 73, which are a pair of opposing sides that intersect the sides of the two sealed end portions and extend in the wrapping direction on the body being examined.

The partial welded portions 79A, 79B, 81A, and 81B are formed at discrete positions toward respective ends of the long sides 71 and 73 relative to a central region 83 in the wrapping direction of the air bladder 23A.

More specifically, the air bladder 23A is formed into a rectangular shape with a pair of opposing sides as the long sides and a pair of opposing sides that extend in a direction orthogonal to the wrapping direction as the short sides. The partial welded portion 79A is formed in a first end portion region AL1, which is to one side of the central region 83 on the long side 71, and the partial welded portion 79B is formed in a second end portion region AR1, which is to the other side of the central region 83. Also, the partial welded portion 81A is formed in a first end portion region AL2, which is to one side of the central region 83 on the long side 73, and the partial welded portion 81B is formed in a second end portion region AR2, which is to the other side of the central region 83.

In the present configuration example, the partial welded portion 79A is formed at a boundary position between the central region 83 and the first end portion region AL1, and the partial welded portion 79B is formed at a boundary position between the central region 83 and the second end portion region AR1. The partial welded portion 81A is formed at a boundary position between the central region 83 and the first end portion region AL2, and the partial welded portion 81B is formed at a boundary position between the central region 83 and the second end portion region AR2.

Also, the partial welded portions 79A, 79B, 81A, and 81B are formed at mutually different positions along the wrapping direction (direction along the long sides). As described above, the partial welded portions 79A, 79B, 81A, and 81B are formed at positions biased toward the vicinity of the two end portions, outside of the central region 83 on the long sides 71 and 73 so that the measurement site can be pressurized with sufficient force.

Regarding the central region 83, which extends equal distances from a central line Lc indicating the center of the long side of the air bladder 23A to the short sides 75 and 77, formation of the partial welded portions in the central region is avoided, and thus the central portion of the air bladder 23A is not prevented from inflating. In the present configuration example, the partial welded portions 79A, 79B, 81A, and 81B are provided near the central region 83 and not in the central region 83, and therefore a pressurizing area for the portion of the body being examined that is to be pressurized the most can be sufficiently ensured.

The partial welded portions 79A and 79B of the present configuration example are formed at a distance La from the center line Lc, and the partial welded portions 81A and 81B are formed at a distance Lb, which is longer than La, from the center line Lc. The central region 83 extends in a trapezoidal shape, and the long side 73, which is to be the longer bottom side, is arranged on the proximal side (side near the torso) of the body being examined. Also, the shorter long side 71 is arranged on the distal side (side away from the torso) of the body being examined.

Figure 7:
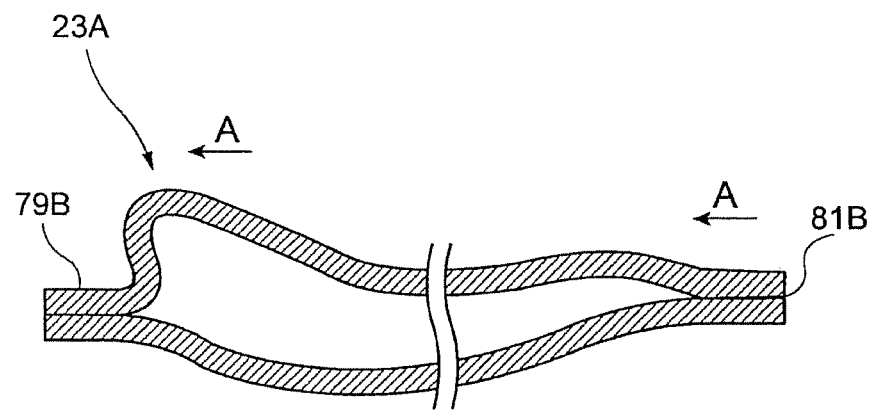
FIG. 7 is a schematic cross-sectional view of the air bladder shown in FIG. 6, taken along line Q-Q.
Figure 12A:
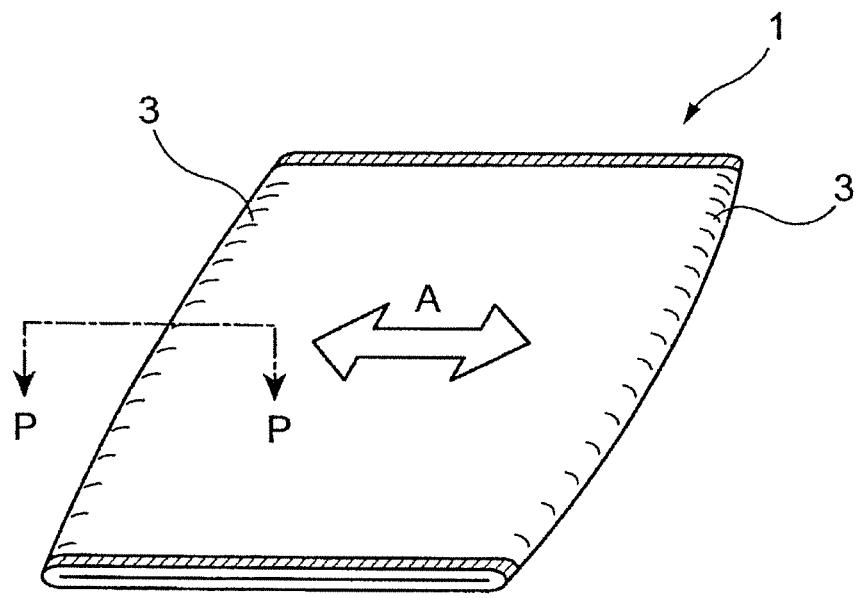
FIG. 12A is a diagram illustrating issues with a cuff having a conventional structure.
Figure 12B:
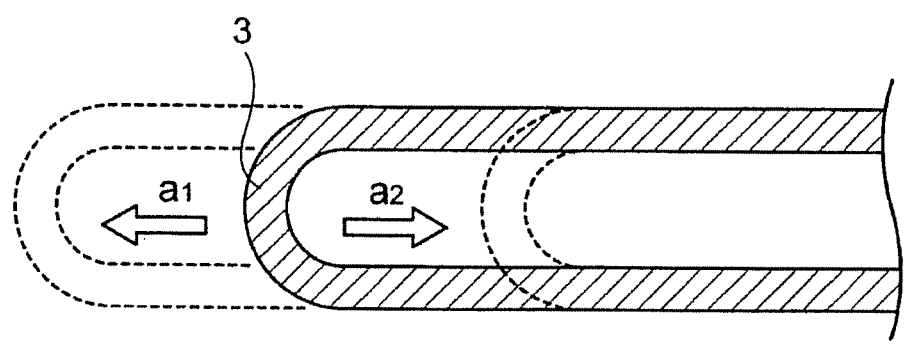
FIG. 12B is a diagram illustrating issues with a cuff having a conventional structure.

For this reason, when air is injected into the air bladder 23A so as to cause expansion and pressurize the measurement site, the partial welded portions 79A, 79B, 81A, and 81B prevent lateral shifting along the short sides 75 and 77 of the air bladder 23A. As shown in the schematic cross-sectional view taken along line Q-Q of the air bladder 23A in FIG. 7, even if an external force A is applied to the air bladder 23A, the partial welded portion 79B prevents extension in the direction a1 shown in FIG. 12, and the partial welded portion 81B prevents retraction in the direction a2 shown in FIG. 12B.

Accordingly, in the case of expanding the air bladder 23A, it is possible to cause a sufficient pressurizing force to be applied stably without shifting from the measurement site. An effect of preventing lateral shifting can be obtained in both a period from when the air bladder 23A starts to expand with the supply of air to the air bladder 23 to when the expansion is complete, and a period in which the expanded state is continuously maintained.

Note that it is preferable that a welding margin width W3 in a direction orthogonal to the sides (long sides 71 and 73) on the outer edges of the air bladder 23A is narrower than a welding margin width W1 from the edge portion of the first welded portion 61 and a welding margin width W2 from the edge portions of the second welded portions 65 and 67. By making the welding margin width W3 narrower, it is possible to minimize the influence thereof on the expansion of the air bladder 23A.

The shape of the partial welded portions 79A, 79B, 81A, and 81B is not limited to the rectangular shape in the example shown here, and it is possible to use another shape.

Figure 8A:
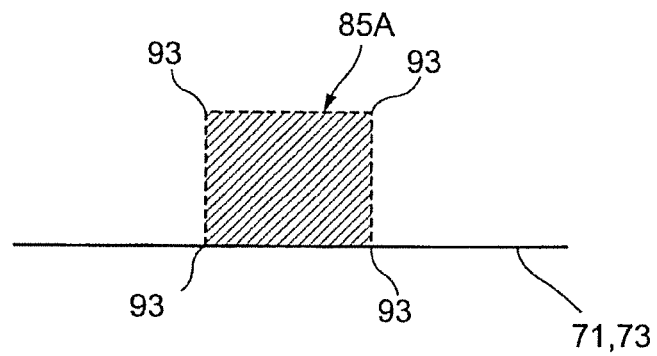
FIG. 8A is a plan view showing a variation of the shape of a partial welded portion.
Figure 8B:
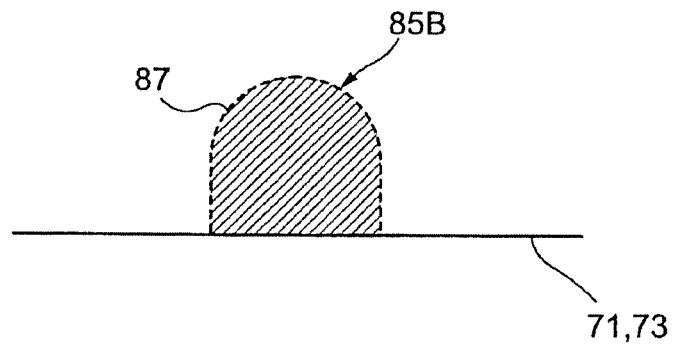
FIG. 8B is a plan view showing a variation of the shape of a partial welded portion.
Figure 8C:
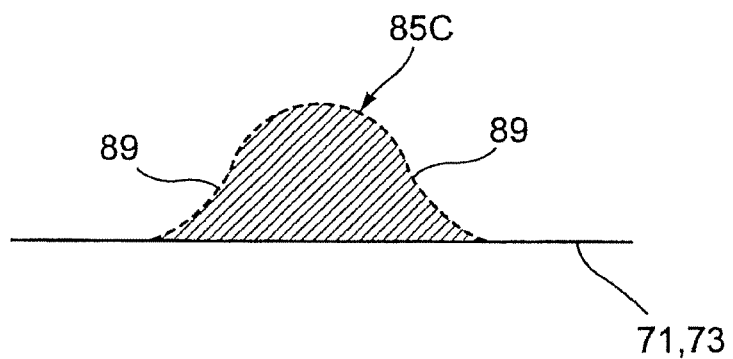
FIG. 8C is a plan view showing a variation of the shape of a partial welded portion.
Figure 8D:
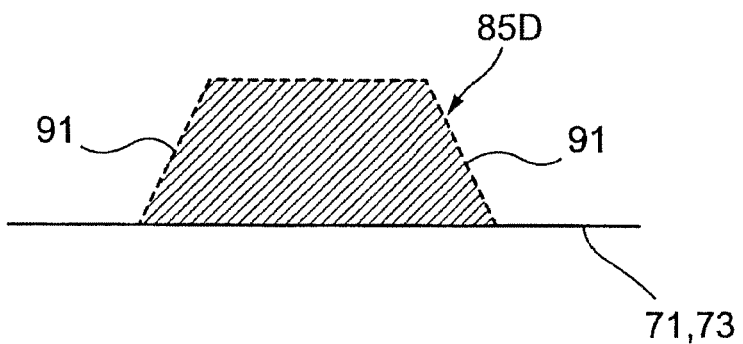
FIG. 8D is a plan view showing a variation of the shape of a partial welded portion.

FIGS. 8A, 8B, 8C, and 8D are plan views showing variations of the shape of the partial welded portions. FIG. 8A shows the case of a square-shaped partial welded portion 85A, FIG. 8B shows the case of a partial welded portion 85B whose shape includes a semicircular portion, FIG. 8C shows the case of a partial welded portion 85C, which is formed by widening the base of the shape shown in FIG. 8B, and FIG. 8D shows the case of a trapezoidal partial welded portion 85D.

In the case of using a partial welded portion of any shape, the above-described effect can be obtained. Furthermore, in the case of forming the semicircular portion 87 shown in FIG. 8B, base portions 89 shown in FIG. 8C, or trapezoid inclined side portions 91 shown in FIG. 8D, it is possible to mitigate the concentration of stress at a corner portion 93 shown in FIG. 8A at the time of expanding the air bladder 23A, and the durability of the air bladder 23A can be further improved.

The partial welded portions of various shapes are formed at mutually different positions along the wrapping direction on the long sides 71 and 73, which are a pair of opposing sides of the air bladder 23A in the case where the cuff 13 is attached at the measurement site. That is to say, the central positions of the partial welded portions are arranged at different positions with respect to the direction of the short sides 75 and 77 in the case of viewing the air bladder 23A in a plan view. This makes it possible to prevent wrinkles from occurring in the air bladder 23A when the air bladder 23A is expanded.

The positions at which the partial welded portions are arranged and the size of the partial welded portions can be illustrated as follows, with reference to the partial welded portions shown in FIG. 6, for example. If it is assumed that the central region 83 of the air bladder 23A, which corresponds to the region that is to be pressurized the most of the body being examined, is a range of 60 mm with respect to the vicinity of the center line Lc of the air bladder 23A, the partial welded portions 79A, 79B, 81A, and 81B can each be set to be around 3 mm in the circumferential direction (long-side direction) when wrapped around the body being examined, and around 1 mm in the short-side direction, which is orthogonal to the circumferential direction. Also, these rectangular partial welded portions 79A, 79B, 81A, and 81B can be formed at mutually different positions along the long sides 71 and 73, with an interval of 8 mm between the central positions of the welded portions, for example.

Figure 9:
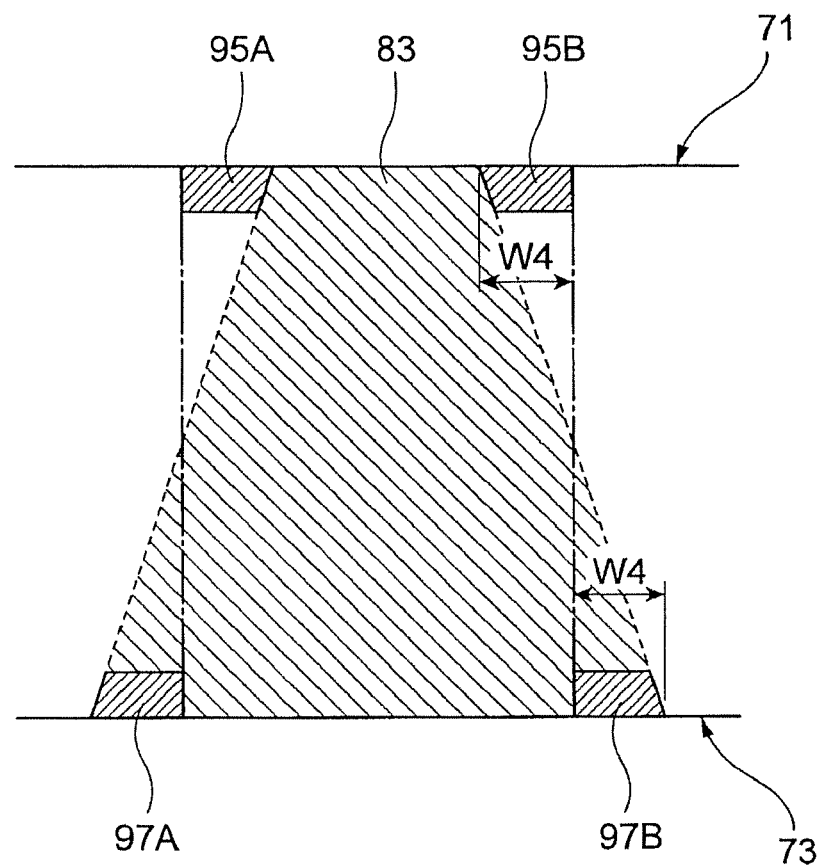
FIG. 9 is a plan view showing a partial welded portion according to a second configuration example.

FIG. 9 shows a modified example of the positions of the partial welded portions.

A configuration may be used in which the partial welded portions are arranged in the vicinity of the central region 83 of the air bladder 23A. That is to say, partial welded portions 95A and 95B shown in FIG. 9 are formed outside of the central region 83, but partial welded portions 97A and 97B may be arranged near the central region 83, or in the central region 83. The partial welded portions 95A, 95B, 97A, and 97B in this case have shapes obtained by bisecting the trapezoidal partial welded portion shown in FIG. 8D, and the trapezoid inclined side portions thereof are each matched with the borderline of the central region 83.

According to the arrangement of the partial welded portions of the present modified example, it is possible to make the long-side width W4 of the welding margin narrower using an arrangement that takes into consideration the tapering of the trapezoid incline portions of the partial welded units 95A, 95B, 97A, and 97B.

Second Configuration Example

Figure 10:
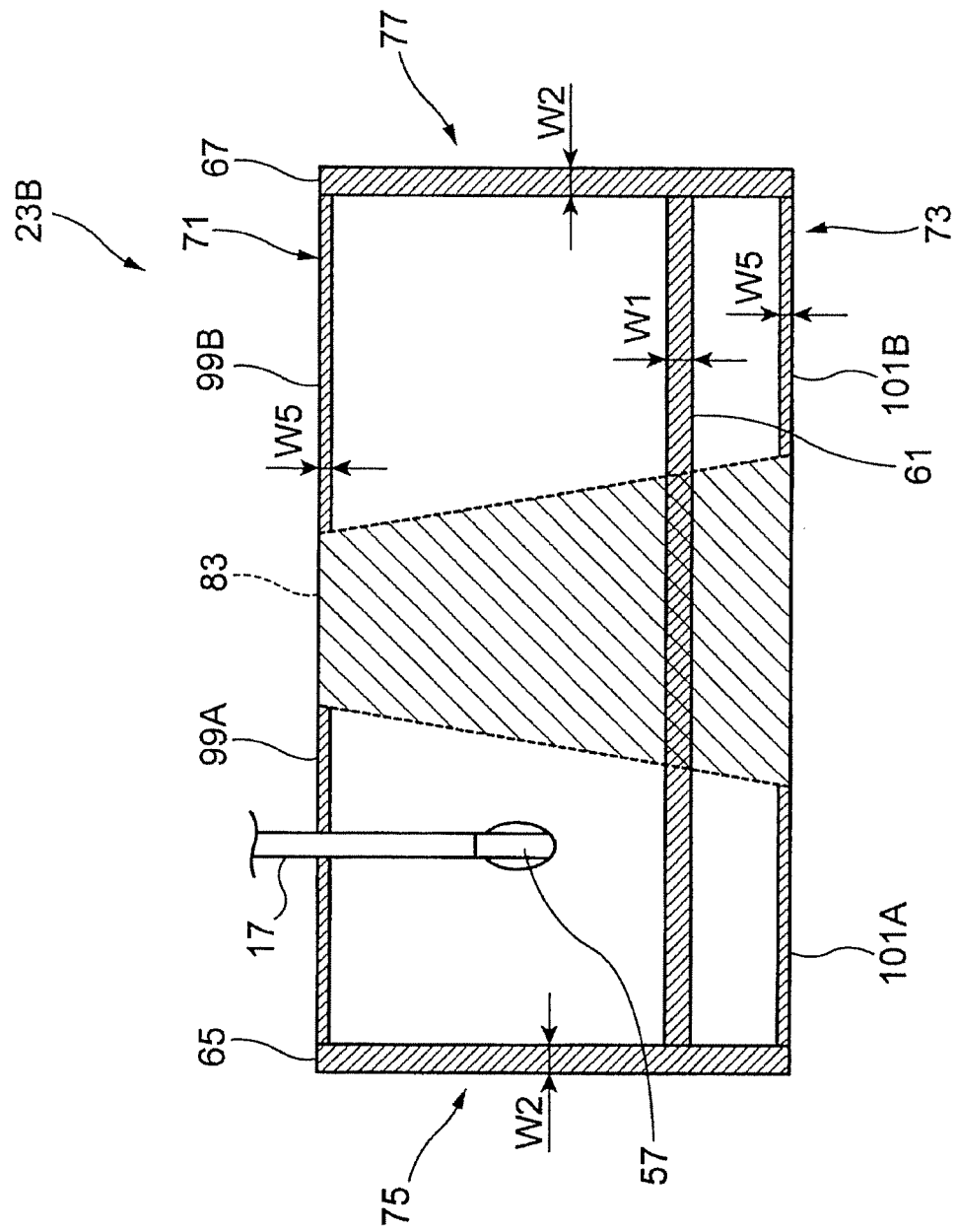
FIG. 10 is a plan view showing a partial welded portion according to a third configuration example.

FIG. 10 is a plan view of an air bladder according to a second configuration example. With an air bladder 23B of the present configuration example, partial welded portions 99A, 99B, 101A, and 101B that are continuous along the long sides 71 and 73 are formed on the long sides 71 and 73 outside of the central region 83. One end of the partial welded portion 99A is connected to the second welded portion 65 on the long side 71 of the air bladder 23B, and the other end extends continuously to the boundary with the central region 83. Similarly, the partial welded portion 99B is connected to the second welded portion 67 and extends continuously to the boundary with the central region 83.

Also, the partial welded portions 101A and 101B are also similarly connected to the second welded portions 65 and 67 and extend continuously to the boundary with the central region 83.

A welding margin width W5 from the edge portions (71, 73) of the partial welded portions 99A, 99B, 101A, and 101B is formed narrower than the welding margin width W1 from the edge portion of the first welding portion 61 and the welding margin width W2 from the edge portions of the second welded portions 65 and 67.

In the partial welded portions 99A, 99B, 101A, and 101B of the present configuration example, the welding margin width W5 is a width that is greater than or equal to 70% and less than or equal to 90% of the welding margin widths W1 and W2. Accordingly, since the partial welded portions can be formed using a simple step, the number of manufacturing man-hours can be reduced and the air bladder 23B can be manufactured at a low cost.

Also, when the air bladder 23B is expanded, according to the continuous partial welded portions 99A, 99B, 101A, and 101B, the occurrence of lateral shifting can be prevented more reliably, and a sufficient pressurization force can be applied to the measurement site.

Third Configuration Example

Figure 11:
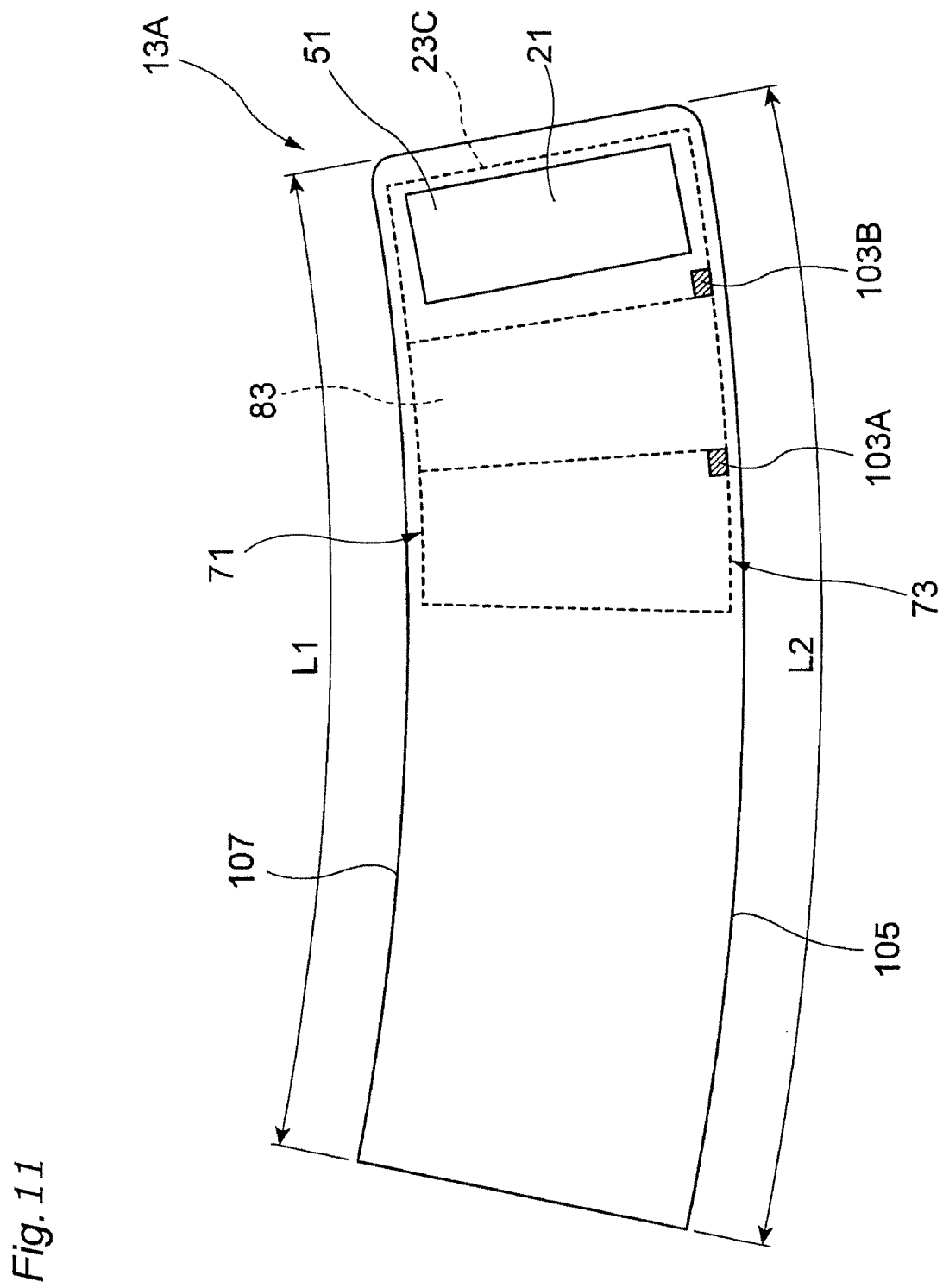
FIG. 11 is a plan view showing a cuff body according to a fourth configuration example.

FIG. 11 is a plan view showing a cuff in a third configuration example. In consideration of the state of being wrapped around the body being examined, a cuff 13A has a curved belt shape in which one long side 105 is longer than another long side 107. When the cuff 13A is wrapped around the body being examined, the long side 105 is arranged on the proximal side (side close to the torso) of the body being examined, and the shorter long side 107 is arranged on the distal side (side away from the torso) of the body being examined.

In an air bladder 23C contained in the cuff 13A in this case, partial welded portions 103A and 103B are formed only on the long side 73 arranged toward the long side 105 of the cuff 13A, and no partial welded portion is formed on the long side 107 located on the opposite side.

According to the above-described configuration, the partial welded portions are arranged at the minimum necessary number of positions, and therefore the expansion of the air bladder 23C is not inhibited, and a sufficient pressurization force can be applied to the measurement site. Note that a configuration is possible in which partial welded portions with welding margins that are narrower on the long side 107 than on the long side 105 are formed on the air bladder 23C. For example, if the welding margin width from the edge portions of the partial welded portions 103A and 103B on the long side 105 is 1 mm, the welding margin width of the partial welded portions on the long side 107 is set to be 0.8 mm, and thereby the welding area of the partial welded portions located toward the long side 105 can be made relatively larger than the partial welded portions located toward the long side 107.

The claimed invention is not limited to the above-described embodiments, and combinations of the configurations of the embodiments with each other, and modifications and applications made by a person skilled in the art based on the description of the specification and known techniques are anticipated with respect to embodiments of the claimed invention and encompassed in the range for which protection is sought. The above-described blood pressure information measurement apparatus has been described using a wrist-type blood pressure information measurement apparatus as an example, but one or more embodiments of the claimed invention are not limited to being wrist-type, and one or more embodiments of the claimed invention may have an apparatus configuration that is applicable to any of the four limbs.

The blood pressure information measurement apparatus cuff and the blood pressure information measurement apparatus according to one or more embodiments of the claimed invention are useful when used in a wrist-type blood pressure information measurement apparatus for measuring blood pressure information such as a blood pressure value in a state of being attached to a wrist of the measurement subject, and can apply a sufficient pressurization force to the measurement site with a simple configuration and realize high-accuracy blood pressure measurement.

This application claims the benefit of Japanese Patent Application No. 2012-211137, filed Sep. 25, 2012, which is hereby incorporated by reference herein in its entirety.

REFERENCE NUMERALS LIST

11 Apparatus body
13 Blood pressure meter cuff
23, 23A, 23B, 23C Air bladder
27 Blood pressure measurement air system component
29 Pressure sensor
31 Expansion/contraction mechanism
33 Pump
35 Valve
37 Oscillation circuit
39 Pump drive circuit
41 Valve drive circuit
43 CPU
45 Memory unit
47 Power supply unit
55 Resin sheet
61 First welded portion
63 End of tube-shaped body
65, 67 Second welded portion
71, 73 Long side
75, 77 Short side
79A, 79B Partial welded portion
81A, 81B Partial welded portion
83 Central region
85A, 85B, 85C, 85D Partial welded portion
95A, 94B Partial welded portion
97A, 97B Partial welded portion
99A, 99B Partial welded portion
100 Blood pressure information measurement apparatus
101A, 101B Partial welded portion
103A, 103B Partial welded portion
105, 107 Long side

The invention claimed is:

1. A method for manufacturing a blood pressure information measurement apparatus, the method comprising:
    forming a hole in a flexible resin sheet;
    inserting a connecting pipe into the hole;
    overlaying a first end portion and a second end portion of the flexible resin sheet such that an inner side of the first end portion contacts an outer side of the second portion;
    welding a location at which the first end portion and the second end portion overlap to form a first welded portion, such that the flexible resin sheet forms a tube-shaped body having a first end and a second end;

flattening the tube-shaped body;

welding the first end and the second to form two second welded portions, such that the tube-shaped body forms a bladder having two long sides and two short sides; and welding portions of the resin sheet which overlap along a first long side to form one or more first partial welded portions oriented parallel to a wrapping direction of the bladder, wherein a wrapping direction of the bladder is defined as being parallel to a circumference of a body when the bladder is wrapped around the body.

2. The method of claim 1, further comprising welding portions of the resin sheet which overlap along a second long side to form one or more second partial welded portions.

\* \* \* \* \*